(12) United States Patent
Schiraldi et al.

(10) Patent No.: US 6,313,369 B1
(45) Date of Patent: Nov. 6, 2001

(54) STRUCTURED OCCLUSIVE DRESSING

(75) Inventors: Michael T. Schiraldi, East Brunswick; Nikhil Kundel, Piscataway; Mark Mooney, Somerset, all of NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/503,259

(22) Filed: Feb. 14, 2000

Related U.S. Application Data

(63) Continuation of application No. 09/225,645, filed on Jan. 5, 1999, which is a continuation of application No. 08/281,423, filed on Jul. 27, 1994, now Pat. No. 5,829,226, which is a continuation-in-part of application No. 08/100,088, filed on Jul. 29, 1993, now abandoned.

(51) Int. Cl.$^7$ .................................................. A61F 13/00
(52) U.S. Cl. ........................... 602/41; 602/42; 602/43; 602/44; 602/45; 602/46; 602/47
(58) Field of Search ......................................... 602/41–48

Primary Examiner—Mickey Yu
Assistant Examiner—Lalita M. Hamilton
(74) Attorney, Agent, or Firm—Lawrence D. Schuler

(57) ABSTRACT

This invention relates to a composition containing a hydrophobic solvent, a network polymer and a flow control agent which is useful in healing wounds. The composition of this invention may be applied directly to a wound to create a structured occlusive dressing. The dressings of this invention do not migrate, but maintain their integrity at skin temperature, and encourage the creation of a moist wound environment while protecting the wound in order to accelerate healing.

5 Claims, 5 Drawing Sheets

STRUCTURED OCCLUSIVE DRESSING

This application is a con of Ser. No. 08/225,645 filed Jan. 5, 1999, which is a con of 08/281,423 filed Jul. 27, 1994 now U.S. Pat. No. 5,829,226, which is a CIP of Ser. No. 08/100,088 filed Jul. 29, 1993 abn.

FIELD OF THE INVENTION

This invention relates to a structured wound dressing which remains in place and does not flow, but has an ointment-like feel.

BACKGROUND OF THE INVENTION

For many years, people have cared for wounds or other skin insults using absorbent bandages as coverings. It is well-documented ("Epidermal Wound Healing", H. I. Maibach, D. T. Rovee, editors, YearBook Medical Publishers, Inc. 1972) that wounds heal faster when covered and kept moist while being protected from additional abrasion and exposure.

In order to protect the wound further from becoming infected, some individuals apply antiseptic or antibiotic agents to the wound prior to bandaging. These medicinal agents may be applied in the form of a liquid, or a water-in-oil emulsion such as an ointment or cream. However, these formulations tend to run, in the case of liquids, or ooze out from under the bandage. Thus, maintaining the position of the medicinal agent in close proximity to the wound in order to impart medicinal activity to the wound is quite difficult. It would be desirable for such consumers to be able to apply a medicament which will not migrate from the wound, i.e., a "structured" dressing.

This object, however, is quite difficult to achieve. For example, many of the ointments used in antiseptic and antibiotic formulations are petroleum-based. However, by their nature, ointments, particularly ointments based on petrolatum, flow fairly easily. Consumers feel comfortable using such petrolatum-based products and are accustomed to the sensation of wearing the ointment in conjunction with adhesive bandages. Thus, any attempt at creating a stable, "structured" base for medicinal application should have an ointment "feel".

Many individuals apply adhesive bandages to their smaller cuts and abrasions. Similarly, they apply gauze or other types of coverings to larger skin wounds. It would be highly desirable for such wound-coverings to have, incorporated within their structures, medicinal agents to combat wound infection. This would afford consumers a great convenience. Conventional ointments and petrolatum-based formulations tend to be too runny and messy for incorporation with a wound-covering material.

Therefore, it is an object of this invention to provide a structured material which can serve as a base for maintaining a covering over a wound.

It is another object of this invention to provide a structured material which can serve as a base for maintaining an occlusive covering over a wound.

It is another object of this invention to provide a wound dressing having an antibiotic or antiseptic agent incorporated in its structure.

Yet another object of this invention is to provide a structured material which can serve as a base for applying medicaments to a wound.

Still another object of this invention is to provide a pressure sensitive adhesive coated material which can serve as a base for maintaining in place the structured wound dressing.

A further object of this invention is to provide a structured material for use in a wound-dressing that has an ointment-like feel but which retains its position over a wound without flowing.

Yet another object of this invention is to provide a structured material for use in a wound-dressing that adheres to intact skin yet easily releases from an open wound without retraumatizing the wound.

Additional objects will become evident in the ensuing description of the invention.

SUMMARY OF THE INVENTION

This invention relates to a composition containing a hydrophobic solvent base and a combination of polymers which create a structured occlusive dressing having a high viscosity and an ointment-like feel.

More particularly, this invention relates to a composition containing a hydrophobic solvent base, a network polymer and a flow control polymer which results in a high-viscosity, structured dressing. Due to its high viscosity and its hydrophobicity, the structured dressing of this invention is believed to provide unique drug delivery characteristics. It permits the addition of drugs to the dressing which may otherwise be irritation-producing but, in the dressing of this invention, do not irritate the skin.

The structured occlusive dressings of this invention may be applied directly to the skin, or they may be incorporated into a combination dressing and be attached directly to a substrate such as a covering material or bandage. The covering material may be a woven or nonwoven fabric or a film material, or a combination thereof.

DETAILED DESCRIPTION OF THE PREFERRED EMBODIMENTS

Figure 1:
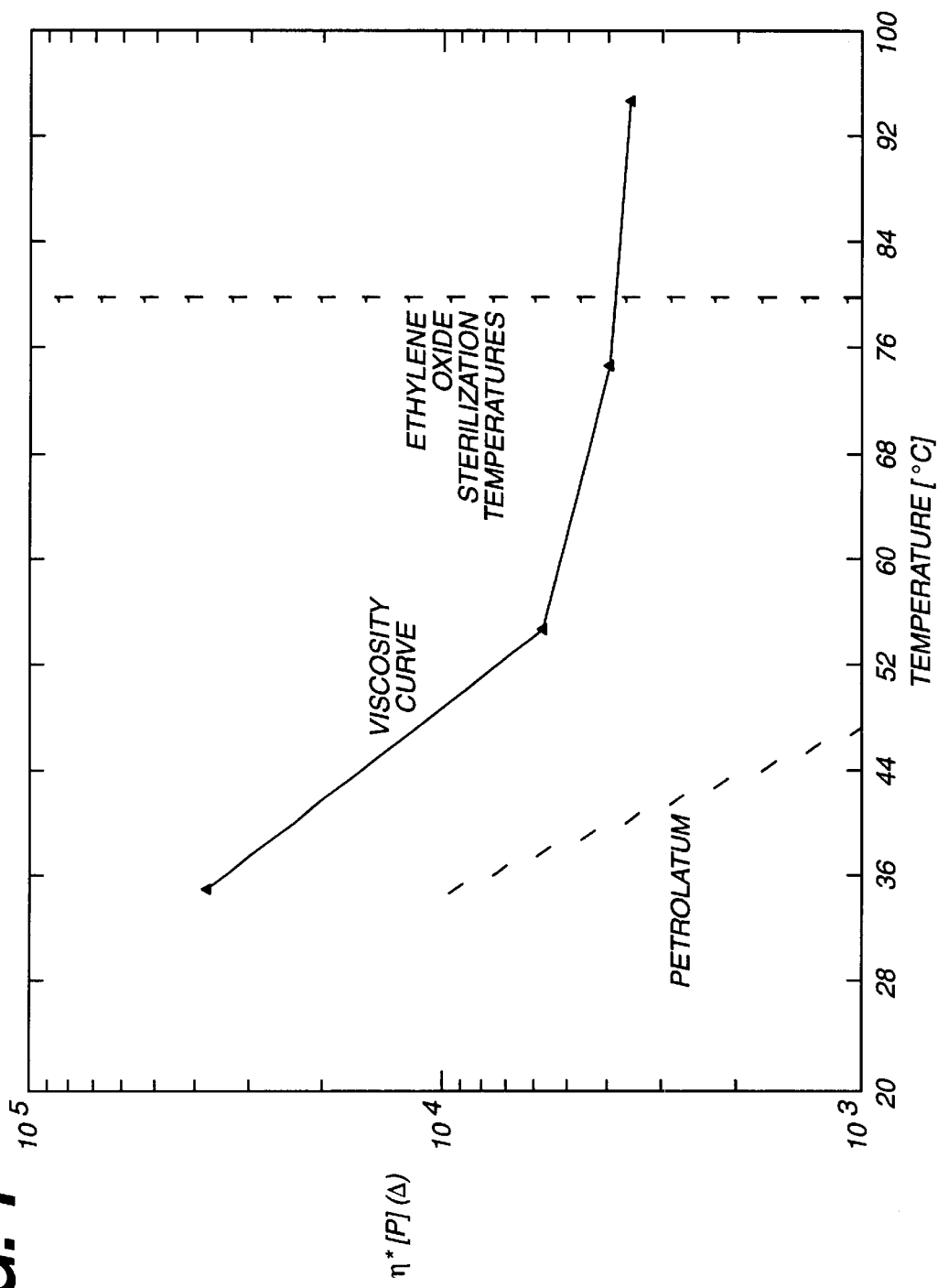
FIG. 1 is a plot showing viscosity as a function of temperature for petrolatum and for one of the occlusive compositions of the present invention.

The compositions of this invention generally contain a hydrophobic solvent or a combination of hydrophobic solvents and other additives resulting in a structured dressing that does not readily flow. The structured dressings of this invention may be an oil-phase composition or a water-in-oil emulsion.

The hydrophobic solvent may be a hydrocarbon material, such as petrolatum, mineral oil or the like. It may also be composed of fatty acids such as castor oil or similar material. Alternatively, the hydrophobic solvent constituent may contain a wax in addition to other solvents, such as paraffin wax, microcrystalline wax, beeswax or the like. This element of the composition serves as the "oil base" of the solvent or the emulsion and makes up a large proportion of the composition, up to 90%. This solvent imparts the ointment "feel" to the composition. The solvent also provides occlusion, contributes to the regulation of drug delivery and is the primary means by which the dressings of this invention achieve superior wound-release characteristics. Preferably, it is a fluid, semi-solid or solid at room or skin temperature (from about 50° F. to about 100° F.) having a viscosity of from about 1 to about 100,000 centipoise. Thus, any hydrocarbon material or combination of materials which have the appropriate viscosity at the desired temperatures may be used in the products of this invention.

A combination of members of two classes of polymers and/or additives should be added to the hydrophobic solvent to make the compositions of this invention. The first class of polymers can be generally termed "network" polymers. These polymers increase the viscosity of the solvent or emulsion and provide gel strength to the solvent or emulsion. The second class of polymers can be generally termed "flow control" polymers, which assist in controlling the flow characteristics of the dressings of this invention.

Gel strength can be measured by the relationship between the viscosity of the composition and temperature. Network polymers show a "plateau" in this type of measurement, i.e., the viscosity of the composition displays little or no change over a wide temperature range. The value of the viscosity at this plateau is defined as the gel strength. Preferably, in the compositions of this invention, the gel strength should be from about 1000 to about 10,000 poise over a temperature range of from about 50° C. to 95° C.

Gel strength is particularly important in manufacturing and processing sterile bandages and wound dressings. The products are often subjected to ethylene oxide sterilization processes at high temperatures (about 175–180° F., 80–82° C.). The products of this invention should be able to withstand such temperatures without causing the structured ointments of this invention to flow readily into the primary packaging or into the pressure sensitive adhesive. Such ready flow would compromise sterility or affect the ability of adhesive to adhere to skin.

Preferably, the polymers that are useful in the compositions of this invention to create gel strength are block copolymers. Di-, tri- and multiarm block copolymers of polystyrene and synthetic rubber where the rubber is preferably isoprene, ethylene butadiene, ethylene propylene or the like or combinations thereof are useful as network polymers in the dressings of this invention. Examples of such polymers are Kraton® di- and tri-block copolymers commercially available from the Shell Chemical Company and the like. The Kraton® polymers are described by the Shell Chemical Company as elastomers which have a combination of high strength and low viscosity. These polymers contain block segments of styrene monomer units and rubber monomer units.

Polyacrylic acids which are slightly crosslinked such as the Carbopols®, commercially available from B. F. Goodrich, are also useful as network polymers in the products of this invention. Polyacrylic acids of this type and other polymers such as polyethylene oxide, cellulosics and polysaccharides act as network polymers and may also contribute to maintaining moisture in the wound. The Aquasorb-D series from Hercules Corporation, which is modified quar gums are examples of modified polysaccarides which are useful in the compositions of this invention by maintaining gel strength. Preferably, one Carbopol® polyacrylic acid that would be useful in the compositions of this invention is 934P. It contains the following monomers: acrylic acid monomers with alkyl sucrose as the crosslinker.

The second class of polymers or additives useful in the compositions of this invention are the "flow control polymers", which are chosen to assist in controlling flowability in processing the structured ointment at or about room temperature and film-forming capacity. This lends a more film-like structure to the dressings of this invention as opposed to a gel-like structure. Film-like characteristics are important so as to lend greater integrity at usage temperatures. However, the flowability should not be so great as to permit the compositions to migrate from their desired positions in use on a wound.

The second class of agents, polymers or additives useful in the compositions of this invention also assist in achieving an "ointment feel" to the dressings of this invention. This "ointment feel" can be quantified as the value of the shear elastic compliances and loss compliances of the compositions measured at skin temperatures, (approximately 35° C.) at a testing frequency of 10 radians/second as measured on a Rheometrics RDS 7700 rheometer.

Petrolaturm, for example, has a very high shear compliance, greater than $5\times10^{-5}$ cm$^2$/dyne and has a loss compliance greater than $1\times10^{-5}$ cm$^2$/dyne. Though petrolatum has an "ointment feel", it is also extremely fluid and therefore unacceptable for use by itself in the dressings of this invention. The balance of "controlled flow" and "ointment feel" falls within the following desirable band of shear compliances: the elastic compliance ranges from about 2 to about $20\times10^{-6}$ cm$^2$/dyne and the loss compliance ranges from 3 to $20\times10^{-5}$ cm$^2$/dyne. Above this range, the formulation may have an ointment feel, but its flowability is very high. The desired balance of controlled flow and ointment feel is present within this range. Below this range, the flow is well-controlled, but the composition has a considerably reduced ointment feel.

Preferably, the flow control polymers assist in assuring that, at low temperatures, the viscosity dependence of the compositions of this invention is linear on a log-log plot. This indicates that the compositions of this invention have a controlled, predictable attribute at low, usage temperatures.

Those polymers that assist in controlling flow at low temperatures may be selected from polymers such as polyolefins. Preferably, they are homopolymers, copolymers or polymers composed of several monomers and are not crosslinked. More preferably, this second class of polymers or additives includes the following: ethylene vinyl acetate, or polyalkylenes such as polyisobutylene, ethylene propylene copolymers, polyethylenes and the like. Flow control additives may also preferably be a stearate or palmitate ester, such as a alcohol ester of a fatty acid. Preferably, such an additive may be stearyl alcohol. This class of polymers or additives may also be used to impart some "stickiness" to the composition or may even detackify the composition, depending upon the polymers chosen and their concentrations. For example, polyethylenes added at a concentration of at least 5% may aid in detackifying a composition whereas ethylene vinyl acetate added at a concentration of at least 5% may increase the tackiness of the composition.

Additives may be introduced into the compositions of this invention to influence the "feel" of the final product. The composition should mimic the sensation of ointment products as fully as possible, in order to ensure that the consumer who is accustomed to prior ointment products is comfortable wearing the composition. For example, silicone waxes, common emollients known to those of skill in the art (i.e., polyethylene glycol esters), most preferably, emollients having a stearate or palmitate functional end-groups or the like may be used for this purpose in the dressings of this invention. Dow Corning 580 wax available from Dow Corning, a stearoxy trimethyl silane polymer enhances the ointment feel of the composition by reducing the drag created by the addition of the network and flow control polymers.

Other compounds may be added to the compositions of this invention to increase its hydrophilicity and, still assist in wound healing by maintaining a moist wound environment. For example, castor oil, wool wax alcohol, glycerin, polyethylene glycols, block copolymers of polypropylene oxide and polyethylene oxide and propylene glycol. These compositions absorb a certain amount of water and/or wound fluids, although the rate of absorption is relatively slow. The slow rate of absorption allows the composition to be considered occlusive and, therefore, beneficial to wound healing.

Other compounds may also be added to the compositions of this invention to lend medicinal properties to the product or otherwise cause modification. For example, antispetics, antibiotics, anesthetics or other medicaments may be added to the composition to assist in wound-healing. Examples of such compounds are: neomycin sulfate, polymixin-B sulfate, zinc bacitracin, benzalkonium chloride, cetylpyridium chloride, lidocaine, benzocaine, silver sulfur diazine, hydrocortisone and the combinations thereof and the like. Likewise, skin care agents and therapeutics may be added to the compositions of this invention, for example, retinoid compounds such as tretinoin, retinol, retinaldehyde or the like, alpha hydroxy acids or other products that are well-known.

Preferably, the hydrophobic solvent base should be present in the dressings of this invention in an amount from about 50 to about 95% by weight of the composition; more preferably, they should be present in an amount from about 65 to about 85% of the composition; most preferably, they should be present in an amount from about 75 to about 85% of the composition.

The network polymers should be present in the dressings of this invention in an amount from about 0.5 to about 10% by weight of the composition; more preferably, they should be present in an amount from about 2 to about 8% of the composition; most preferably, they should be present in an amount from about 5 to about 7% of the composition.

The flow control agents should be present in the dressings of this invention in an amount from about 0.5 to about 40% by weight of the composition; more preferably, they should be present in an amount from about 3 to about 20% of the composition; most preferably, they should be present in an amount from about 5 to about 10% of the composition.

The predominantly hydrophobic base, in concert with the structured polymer network reduces the dissolution of the active medicaments in the matrix, thereby slowing their leaving the matrix solution. The predominance of an oil-phase in the structure does not allow the wound fluids to readily leach the active ingredients from the structure. The hydrophobicity prevents the material from being completely bioactive, but rather permits it at a controlled rate. For example, neomycin in a completely hydrophilic environment is 100% bioacitve and totally available to the wound. This can be extremely irritating to the wound and skin. Furthermore, the hydrophobic structure does not readily break down when in contact with the wound bed. A hydrophilic structure would be more soluble in the hydrophilic wound fluid.

The dressings of the invention can be applied directly to a wound, or may be coated directly onto a film or fiber substrate which is, in turn, applied to the wound and surrounding skin. Such films may be composed of one or more of the following polymers: polyethylene, polypropylene, polyesters, poly-vinylacetate. Films useful in the products of this invention may be continuous or discontinuous, i.e., reticulated or having some other regular pattern of "holes".

The dressings of this invention may also be coated onto a fiber substrate which, in turn, is adhesively or otherwise attached to a film substrate. Example of fiber substrates are fabrics that are knitted such as modified entangled fiber composed of rayon polyesters, or those that are woven, such as flexible fabrics composed of rayon-nylon blends. Non-woven fiber substrates may also be used, such as 90:10 polypropylene-rayon blends, or the like. These dressings can be coated onto a film or fiber material and then futher applied to a secondary substrate which holds the dressing in place over the wound. Types of secondary substrates are films or woven or nonwoven fabrics with pressure sensitive adhesives.

The products of this invention are preferably made by blending the constituents in conventional batch mixers such as Brabender Plasticorders, Hobart mixers, Groen mixers, Baker Perkins and the like. Other batch mixers may be used that are capable of applying high shear at elevated temperatures and completely "sweeping" the surface of the bowl or container such that there are no "dead" spots. Continuous mixers may also be used such as Werner Pfleiderer ZSK-30 or American Leistritz ZSE-50. Preferably, the hydrophobic solvent base and optional additives are heated to a suitable temperature, from about 80° C. to about 150° C., prior to addition of the network polymer and flow control polymers. The network and flow control polymers are then blended with the hydrophobic solvent base until they are completely dissolved, i.e. the system is homogeneous and free of gelations. The blend is then preferably coated onto a substrate and cooled to room temperature, resulting in an occlusive structured dressing.

The following examples are merely illustrative of the products of this invention, methods of making such products and methods of using the products. The examples are not intended to limit the scope of the invention.

EXAMPLE 1

To a Brabender Plasticorder heated to 125° C. was added 180 grams of U.S. White petrolatum, 90 grams of Elvax 40 W, a poly-vinylacetate from Dupont, 15 grams of mineral oil and 15 grams of Kraton G 1702, a diblock copolymer from the Shell Company composed of polystyrene and ethylenepropylene copolymer. This composition was mixed for 60 minutes and then the temperature was dropped to 80° C. and mixing was continued for another 30 minutes. The formulation was coated onto a nonwoven substrate while still warm (at 80° C.) using a draw down method. Squares approximately ¾inch in length were centered onto a ¾" by 3" adhesive strip. A release film with a low release surface was placed onto the strip covering the adhesive the ointment surface. The strips were subjected to a standard ethylene oxide sterilization cycle (30 minutes at 175° F.) in the presence of water. No oozing or flowing out of the ointment from the adhesive strip was observed. No ointment was seen on the adhesive strip Referring to FIG. 1, the ethylene oxide sterilization temperature is indicated as a vertical dashed line intersecting the "gelling plateau" region of the viscosity plot, thus indicating that the composition is stable at the temperature and unlikely to flow. In comparison, there is also a dashed line indicating the viscosity-temperature relationship for petrolatum. As indicated by the dashed line, petrolatum would flow readily at about 48° C., far lower that the sterilization temperature. In fact, petrolatum melts at 55° C. and, therefore, would be unacceptable in the products of this invention.

EXAMPLE 2

Using the method of example 1, 210 grams of White Petrolatum, 60 grams of Elvax 40 W, 15 grams of Kraton G1702 and 15 grams of Lanolin Alcohol were coated onto a nonwoven substrate. No oozing or flowing of the ointment was also observed. The composition was tested for hydrophilic properties by the observation of the slow absorption of water droplets placed on the coating of this example.

EXAMPLES 3–6 AND COMPARATIVE EXAMPLE A

The following five compositions were made according to the method of example 1 and also coated onto a nonwoven substrate.

| Compound | 3 | 4 | 5 | 6 | A |
|---|---|---|---|---|---|
| Kraton G 1702 | 11.1 | 7.7 | 11.5 | 11.1 | — |
| Petrolatum | 74.1 | 76.9 | 77.0 | 74.1 | 83.3 |
| Elvax 40W | 14.8 | 15.4 | 11.5 | 11.1 | 12.5 |
| Elvax 150W | — | — | — | 3.7 | 4.2 |

Figure 2:
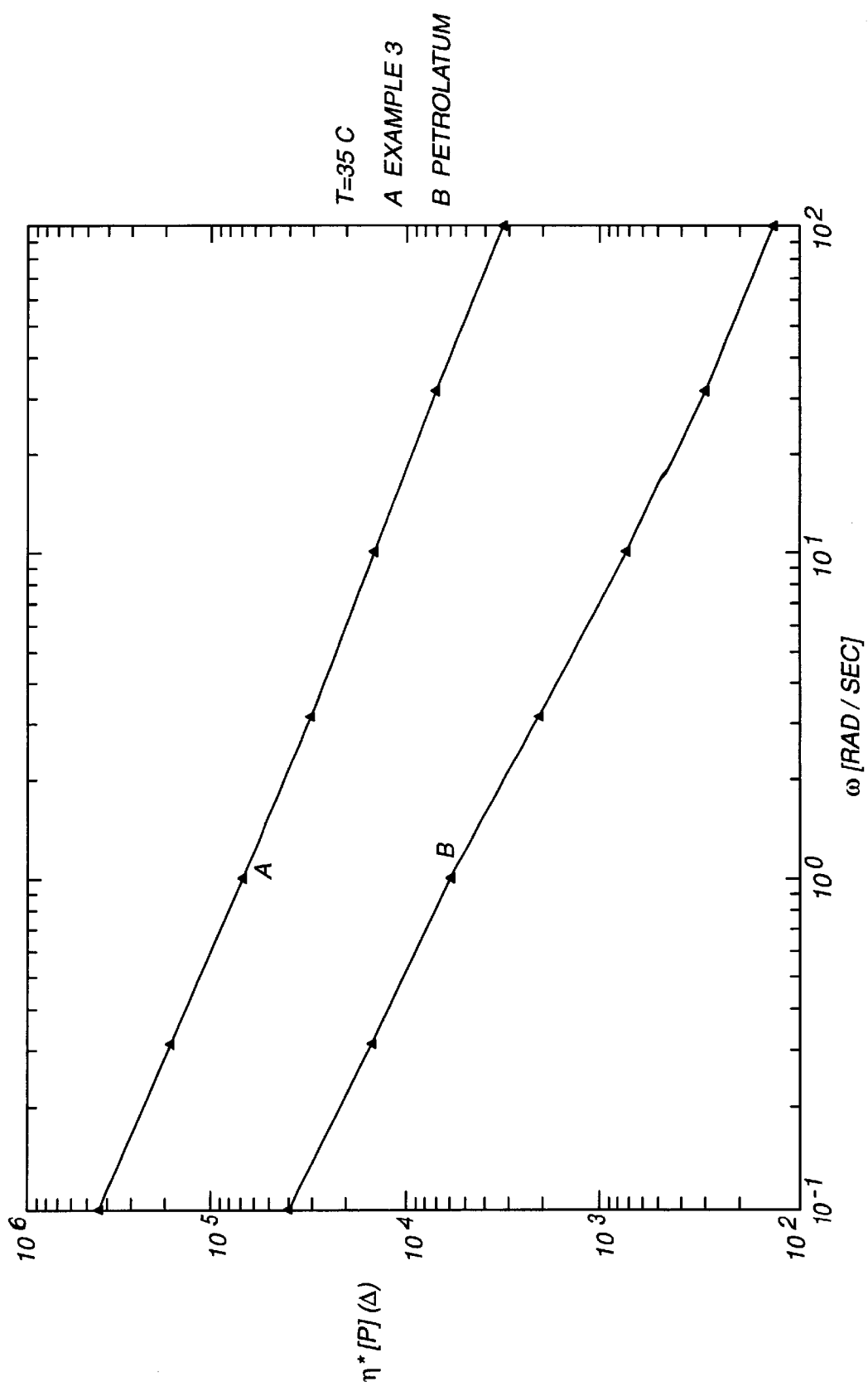
FIG. 2 is a plot showing viscosity as a function of shear rate for petrolatum and for another of the occlusive compositions of the present invention.

The viscosity of the composition of Example 3 as a function of shear rate was measured on a Rheometrics RDS 7700 rheometer at 35° C. and compared to the viscosity of White petrolatum as a function of shear rate. A graph of the results of this measurement is set forth in FIG. 2. An increase in viscosity of a factor of 10 between the White petrolatum and the composition of Example 3 was noted.

Figure 3:
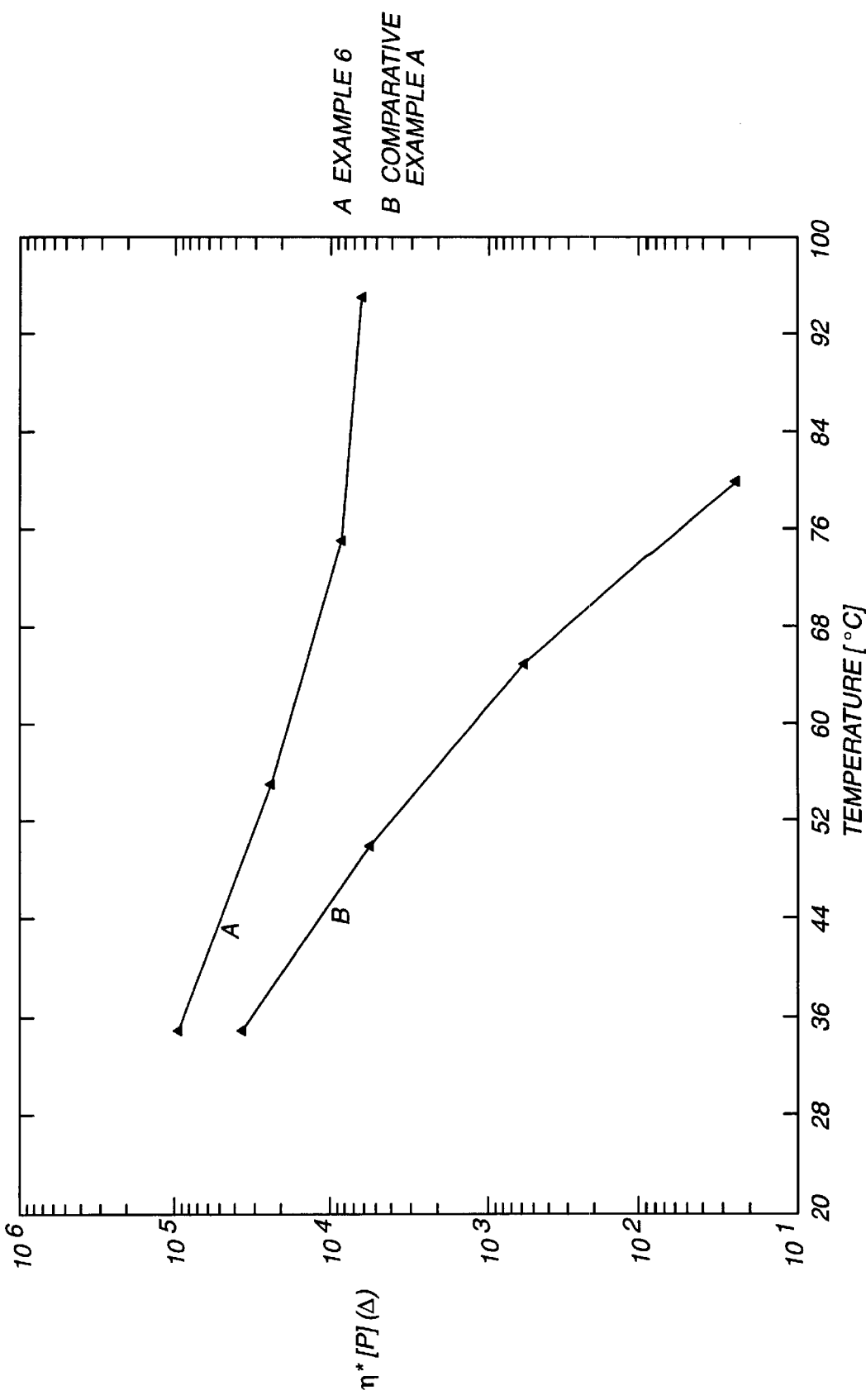
FIG. 3 is a semi-log plot showing viscosity as a function of temperature for yet another occlusive composition of the present invention and a composition (Comparative Example A) prepared for purposes of comparison.

The temperature dependence of the viscosity of compositions of Example 6 and Comparative Example A were compared, the latter containing no "network" polymer. The results of this measurement are set forth as a log-log graph in FIG. 3. As FIG. 3 illustrates, the viscosity-temperature response of Example A is that which would be expected from essentially linear, noncrosslinked polymers in the melt or in solution: on a log-log plot, the relationship between viscosity and temperature over a limited temperature range is linear. However, the relationship for Example 6 is different. As set forth in FIG. 3, at elevated temperatures, the viscosity plateaus. This is what would be expected from a slightly crosslinked or network polymer or a di-or tri-block copolymer. This plateau is called the gelling region; a fairly stable gel or network is apparent at these temperatures. The network is destroyed only at extremely high temperatures.

EXAMPLE 7 AND COMPARATIVE EXAMPLE B

| | 7 | B |
|---|---|---|
| Kraton G1702 | 10.0 | 10.7 |
| USP White Petrolatum | 83.3 | 89.3 |
| Elvax 40W | 6.7 | — |

Figure 4:
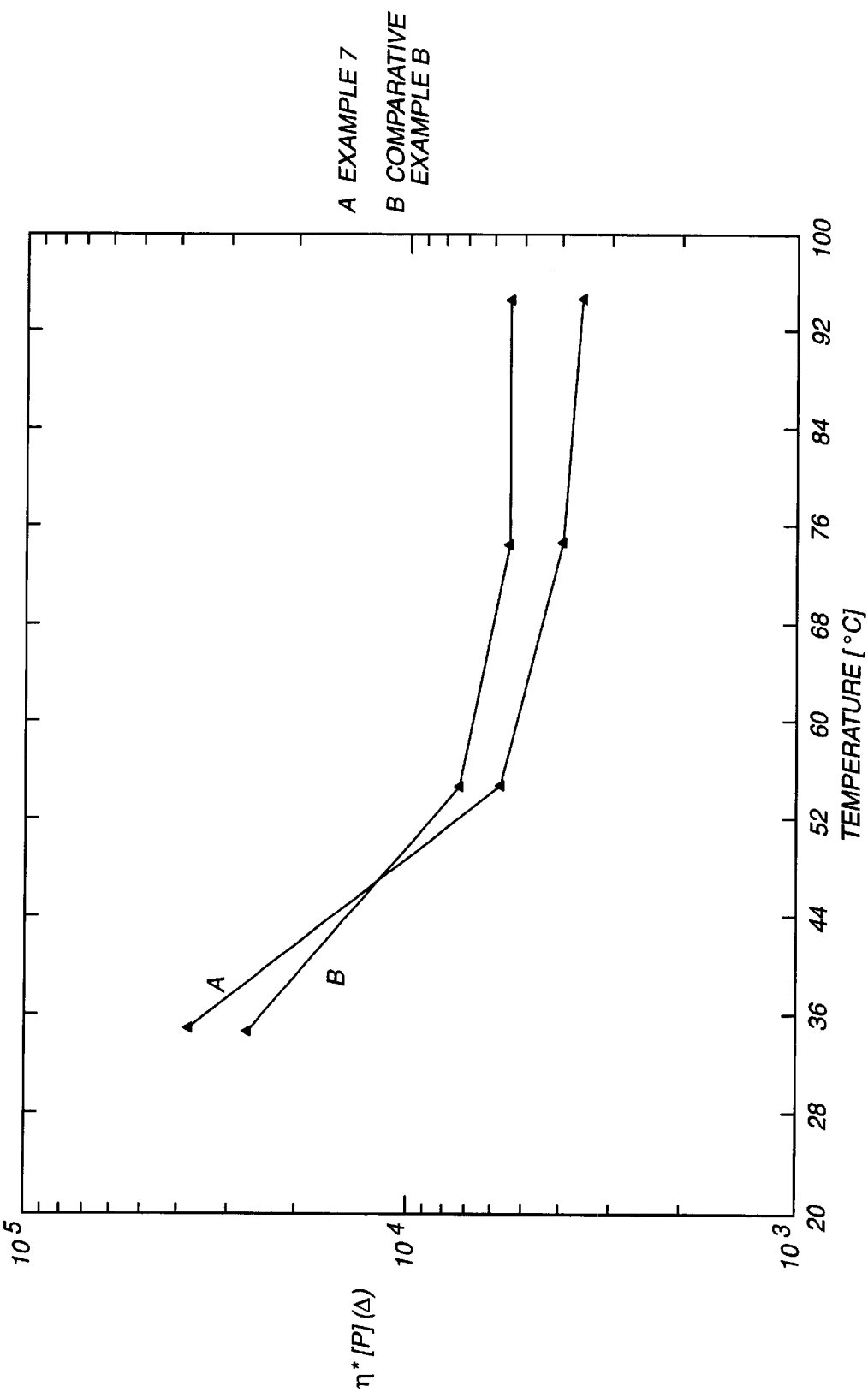
FIG. 4 is a semi-log plot similar to that shown in FIG. 3.

Example 7 was made in accordance with the process described in Example 1 and contains a network polymer, Kraton G1702, petrolatum and a linear polymer, Elvax 40 W, which is a poly-vinylacetate. Example B does not include a linear polymer. Comparisons were made between Example 7 and Comparative Example B using the same method as set forth in Examples 6 to 9. In FIG. 4 at low temperatures, Example 7, which has a total polymer content of 16.7%, has a higher viscosity than Comparative Example B with a total polymer content of 10.7%. As the temperature increase, the viscosity curves "crossover"; i.e., both sets of data exhibit the gelling plateau, but comparative Example B has a higher plateau viscosity than Example 7. This data indicates that the gelling or network polymer has an important influence at elevated temperatures and the linear polymers find its significance at lower temperatures.

EXAMPLES 8–12

Hydrophilic compositions of this invention were made in accordance with the procedure set forth in Example 1. The following compositions were made:

| Compound | 8 | 9 | 10 | 11 | 12 |
|---|---|---|---|---|---|
| Wool Wax Alcohol | 17 g | 12 g | — | — | — |
| Petrolatum | 40 g | 51 g | 69.2 g | 61.5 g | 72.7 g |
| Mineral Oil | 21 g | 10 g | — | — | — |
| Kraton G1702 | 12 g | 12 g | 7.7 g | 7.7 g | 9.1 g |
| Elvax 40W | 10 g | 5 g | — | 7.7 g | 9.1 g |
| Glycerine | — | 10 g | 15.4 g | 15.4 g | — |
| Pluroxide | — | — | .7 g | 7.7 g | 9.3 g |

These compositions exhibited hydrophilic characteristics while maintaining an ointment feel and structured properties. The hydrophilic characteristics were demonstrated by placing a drop of distilled water and timing how long it took for the hydrophilic compositions to absorb water. Typically it took 3–4 minutes. In a comparable test using 100% petrolatum, there was no any perceivable absorption after 30 minutes.

EXAMPLES 13–18

The following compositions were made utilizing the method of Example 1. The figures represent the weight percent of the ingredients set forth below in each composition:

| | 13 | 14 | 15 | 16 | 17 | 18 |
|---|---|---|---|---|---|---|
| Kraton G1650 | 2 | 2 | — | — | 4 | 3 |
| Kraton G1702 | 10 | 7 | 10 | 10 | 5 | 6 |
| USP petrolatum | 88 | 81 | 60 | 70 | 81 | 81 |
| Steroxytrimethyl-silane | — | 10 | 10 | 10 | 10 | 10 |
| Lanolin Alcohol | — | — | 20 | — | — | — |
| Stearyl alcohol | — | — | — | 10 | — | — |

All the above examples provide non-flowing ointment characteristics at elevated temperatures. Esthetics and release from a silicone coated facing paper or adhesion to skin were modified by adjusting ratios of the Kraton diblock and triblock copolymers. Alternatively, additives such as steroxytrimethylsilane or stearyl alcohol enhance release characteristics from the release paper at ambient temperature and reduce greasiness or tackiness of the ointment on skin. All the above formulations are water insoluble with the exception of Example 15, which includes lanolin alcohol that imparts a water absorption characteristic to the base.

EXAMPLE 19

The composition of Example 16 was used as a base for the following triple antibiotic-containing dressing in accordance with this invention.

EXAMPLE 19

|  | % w/w |
|---|---|
| Kraton G 1650 | 2 |
| Kraton G 1702 | 7 |
| Petrolatum, USP | 79.5 |
| Steroxytrimethylsilane | 10 |
| Bacitracin Zinc | 0.80 |
| Polymyxin B Sulfate | 0.13 |
| Neomycin Sulfate | 0.57 |

A concentrate of the active ingredients was made by adding the antibiotic powders into petrolatum at 60° C.; 2.40 Kg of Bacitracin Zinc, 0.39 Kg of Polymyxin B Sulfate and 1.71 Kg of Neomycin Sulfate was dispersed in 50 Kg of US White Petrolatum using a Ross homogenizer set at 60° C. This concentrate was cooled to room temperature. Separately, 6 Kg of Kraton G1650, 21 Kg of Kraton G1702 and 30 Kg of Steroxytrimethylsilane were compounded in 188.5 Kg of USP White Petrolatum in a sweep kettle at 120° C. until complete solution was obtained. This was cooled down to 80° C. and the antibiotic concentrate was added and mixed for 30 minutes and then cooled. The ointment was heated to 60° C. and extruded onto a padstock where it was finished into a complete product. The antibiotic was tested for antimicrobial activity and retained its activity for at least three months.

EXAMPLE 20

Figure 5:
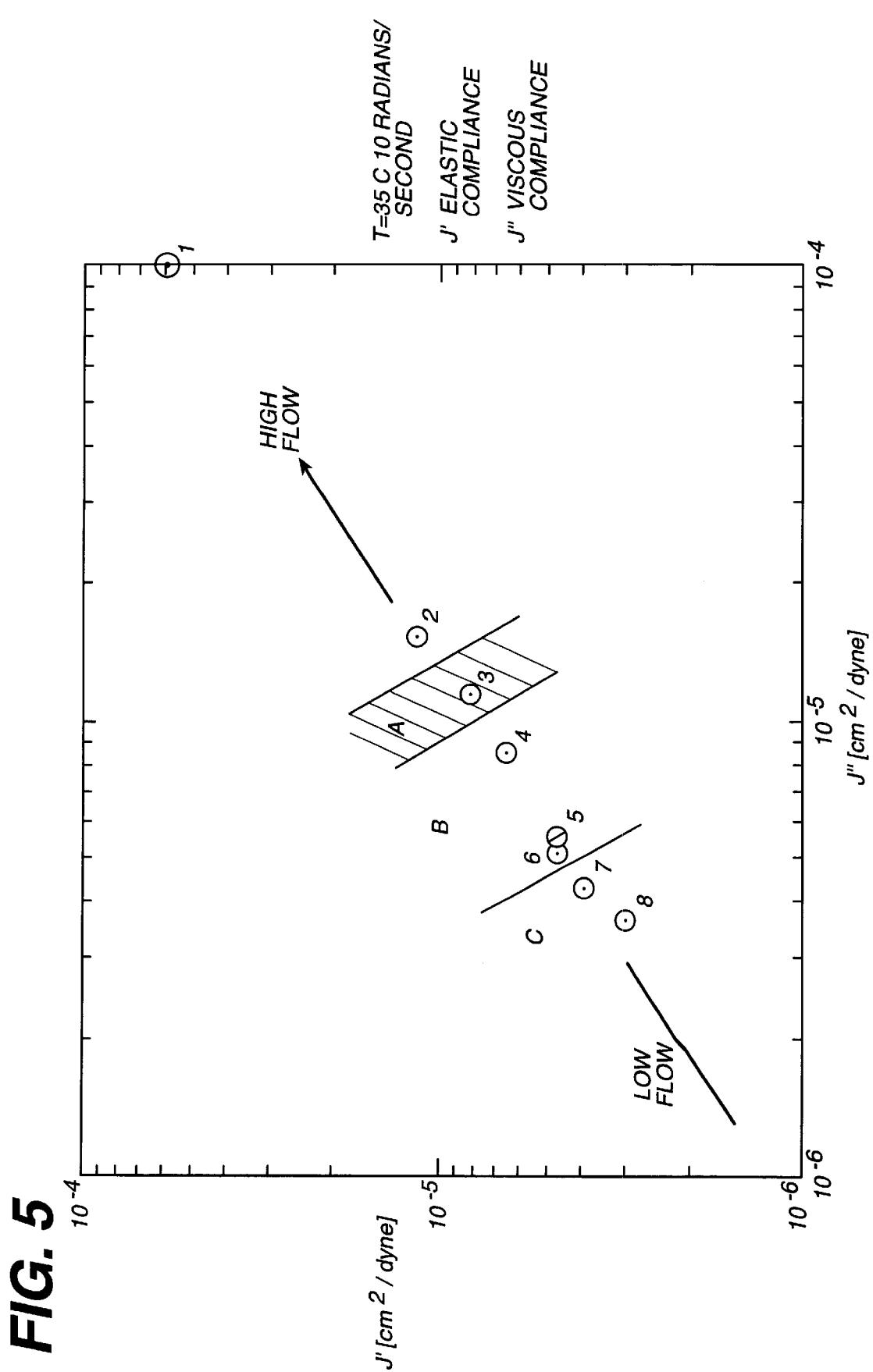
FIG. 5 is a log-log plot showing the shear compliance of petrolatum, six occlusive compositions of the present invention and a composition (Comparative Example B) prepared for purposes of comparison.

The compositions of this invention exhibit a good "ointment feel" while maintaining their integrity during use. FIG. 5 depicts a plot of the elastic compliances and loss shear compliances of compositions of this invention at 35° C. J' represents the elastic shear compliance and J" represents the loss shear compliance. Point 1 represents USP Petrolatum, Point 2 represents Comparative Example B, Point 3 represents Example 7, Point 4 represents Example 14, Point 5 represents Example 18, Point 6 represents Example 6, Point 7 represents Example 17 and Point 8 represents Example 4. The curve indicates the direction of increased flow and soft feel. The area (A), which is shaded, indicates the area of the graph at which products become excessively flowable for use in processing. To the right of the shaded area, the products are too soft for processing. To the left of the shaded area, the products have an ointment feel, but are less flowable and maintain their stability under shear strees. The area marked B represents the preferred balance of controlled flow and "ointment fell"; Example 15 represents such a formula. To the left of B, there is another transition where flow is decreased, which assists the processing of the ointment, but where the desired "ointment feel" is lost. Examples 5 and 6 are at the borderline of acceptability of controlled flow and "ointment feel". In area C the flow is reduced considerably and the "ointment feel" is considerably reduced. Thus, the compositions of this invention exhibit an ointment feel while retaining stability.

What is claimed is:

1. A composition for making a structured dressing comprising:
   a) a hydrophobic solvent base compound;
   b) a network polymer; and
   c) a flow control agent,
said hydrophobic solvent base compound comprising one or more hydrocarbons, said hydrocarbon having a viscosity at 30° C. of from about 1 to about 100,000 centipoise.

2. A composition for making a structured dressing comprising:
   a) a hydrophobic solvent base compound;
   b) a network ploymer; and
   c) a flow control agent,
said composition having a gel strength of from about 1000 to about 10,000 poises over a temperature range of from about 50 to about 95° C.

3. A composition for making a structured dressing comprising:
   a) a hydrophobic solvent base compound;
   b) a network polymer; and
   c) a flow control agent,
wherein said composition has a shear compliance of from about $2 \times 10^6$ $cm^2/dyne$ to about $20 \times 10^6$ $cm^2/dyne$ at a temperature range of from about 55° F. to about 100° F.

4. a composition for making a structured dressing comprising:
   a) a hydrophobic solvent base compound;
   b) a network polymer; and
   c) a flow control agent,
wherein said composition has a loss compliance of from about $3 \times 10^6$ $cm^2/dyne$ to about $20 \times 10^6$ $cm^2/dyne$ at a temperature range of from about 55° F. to about 100° F.

5. A composition for making a structured dressing comprising:
   a) a hydrophobic solvent base compound;
   b) a network polymer; and
   c) a flow control agent,
said flow control agent being selected from the group consisting of fatty acids and said flow control agent is stearoxytrimethylsilane.

\* \* \* \* \*